(12) United States Patent
Ramírez Sabag et al.

(10) Patent No.: US 8,275,549 B2
(45) Date of Patent: Sep. 25, 2012

(54) ONLINE MEASUREMENT SYSTEM OF RADIOACTIVE TRACERS ON OIL WELLS HEAD

(75) Inventors: Jetzabeth Ramírez Sabag, Mexico City (MX); Luis Rubén Amado Hidalgo, Mexico City (MX); Saúl Diaz Jiménez, Mexico City (MX); Marco Antonio Hernández Rojo, Mexico City (MX)

(73) Assignee: Instituto Mexicano del Petroleo, Mexico City (MX)

( * ) Notice: Subject to any disclaimer, the term of this patent is extended or adjusted under 35 U.S.C. 154(b) by 286 days.

(21) Appl. No.: 12/854,599

(22) Filed: Aug. 11, 2010

(65) Prior Publication Data
US 2011/0040484 A1 Feb. 17, 2011

(30) Foreign Application Priority Data
Aug. 12, 2009 (MX) .................... MX/a/2009/008597

(51) Int. Cl.
*G01V 5/04* (2006.01)
*G06F 11/30* (2006.01)
(52) U.S. Cl. ............... 702/8; 702/12; 702/182; 702/188

(58) Field of Classification Search ................ 702/8–13, 702/54–57, 121–123, 182–190
See application file for complete search history.

(56) References Cited

U.S. PATENT DOCUMENTS

| | | | |
|---|---|---|---|
| 4,007,366 A | 2/1977 | Wiley et al. | |
| 4,454,772 A | 6/1984 | Brunner et al. | |
| 4,481,597 A * | 11/1984 | Robbins | 708/5 |
| 5,410,152 A * | 4/1995 | Gadeken | 250/260 |

* cited by examiner

*Primary Examiner* — Phuong Huynh
(74) *Attorney, Agent, or Firm* — Roylance, Abrams, Berdo & Goodman, L.L.P.

(57) ABSTRACT

The online measurement system of radioactive tracers in oil wells head, object of this invention, is characterized by the use of new technology to measure concentrations of tracer activity in real time, using a radiation detector NaI (TI), with features that make it possible to detect up to three different tracers and be able to operate in temperature conditions up to 150° C., which allows to be immersed in a container with fluid coming from the flow stream, achieving with this to increase the sensitivity of the measurements. This system of measurement in the head of production wells will allow having much more data of the tracer activity, avoiding having to transport the operational staff to production wells to carry out sampling test, with all the advantages that this represents.

29 Claims, 3 Drawing Sheets

DETAIL " A "

ONLINE MEASUREMENT SYSTEM OF RADIOACTIVE TRACERS ON OIL WELLS HEAD

CROSS-REFERENCE TO RELATED APPLICATION

This application claims the benefit under 35 U.S.C. §119 of Mexican Patent Application No. MX/a/2009/008597, filed Aug. 12, 2009, which is hereby incorporated by reference in its entirety.

TECHNICAL FIELD OF THE INVENTION

The present invention is concerned with a system for tracers detection which emits gamma radiation at the head of production wells, in order to monitor in real-time concentration values of tracer activity, and that it will be able to operate autonomously according to a monitoring established program, and in this manner to be able to collect more data, which contributes to reduce the uncertainty level and to increase analysis efficiency and interpretation of the results of tracer tests.

BACKGROUND OF THE INVENTION

The main goal during the exploitation phase of an oil reservoir, from a technical-economic point of view, is to obtain the optimal hydrocarbons recovery, so that it remains the least amount of residual oil in the reservoir. In order to increase the amount of oil, it is used the secondary and/or enhanced recovery processes, which mainly consist in injecting fluid for providing additional energy to the reservoir, taking advantage of this energy in the displacement of hydrocarbons towards production wells.

The tracer tests among wells are a widely used tool in the recovery processes, in order to determine the flow trajectories of injection fluids, as well as to detect high permeability zones or drainages that cause a disproportionate distribution of injected fluids, which can be reflected on an efficiency process reduction.

In documents found in tracer tests literature, the sampling test is performed through a visit to the field of selected production wells, by trained technical staff, this task is carried out according to a previously established sampling test program during the design stage of the activities for the tracers injection to the reservoir. This program usually takes into account a high sampling test frequency the days immediately after the tracer injection, so that going down its frequency as long as the time passes through. The reason of high frequency at the beginning is the possibility of the presence of tracer due to drainage which breakthrough the tracer in the production well very quickly. This matter produces a very short tracer response but at the same time of great magnitude so that it can be only possible to reconstituted if it is possible to have a sufficient number of sampling tests. Otherwise, when there is not drainages, the tracer flow more slowly in the porous media, so the scheduling of sampling tests collection is at least one year, and then to accomplish that the tracer response more closely reflect what happens in the reservoir. Taking into account the above description, the cost of the sampling test of a tracers test rises sharply, due to the large amount of sampling tests. It is worth to say that a substantive part of the cost of a tracer project corresponds to the analysis of sampling tests, and often it is sacrificed the number of sampling tests in order to reduce the project costs. However, the information obtained from tracer tests is directly proportional to the number of analyzed sampling tests.

One of the main problems that arise when interpreting a tracers test results, and even, reaching some failure cases, is caused by a poor and/or insufficient monitoring program. This may be due to several factors, mainly to an inadequate program design of the sampling test, or it could also be due to other causes, such as, difficulty of moving through long distances for carrying out the sampling tests, impossibility to perform the sampling tests due to affectations caused by farmers who did not allow access to the wells, remote offshore platforms, or it could also be due to the lack of available resources (human, economics) for sampling tests:

The main advantage that represents the radioactive tracers is the possibility of working with small volumes for its injection and in many cases, especially for gamma emitters, its facility for being detected in-situ. However, the radiation measurements for radioactive isotopes of low energy beta emitters such as tritium (18 keV maximum beta energy) and carbon-14 (155 KeV) are not carried out in the field, because their analysis is carried out with special low level count equipment, therefore all samples are sent for their analysis to specialized laboratories that have liquid scintillation counters equipments. In another case, the use of radioactive isotope tracers that emit gamma radiation, such as: $^{57}$Co, $^{58}$Co and $^{60}$Co, $^{192}$Ir or $^{131}$I, they make much easier their detection, which can be achieved through scintillation crystals. The sodium iodide detectors activated with thallium, NaI (TI), are widely used for the detection of gamma radiation, which given its characteristics make possible that they can be used in the field, which allows it become unnecessary to perform a sampling test and then to send it to the laboratory for radiochemical analysis.

Currently, for measuring gamma radiation, there are a several commercial laptops, however, its use is focused on general applications, among these kind of commercial mobile computers it can be mentioned the following models: 1000 Inspector, Inspector 2000 Canberra brand, and others from the Ortec brand.

It is important to mention that if commercial equipment are intended to be used for detecting radioactive tracers in a intrusive way, which is known by the term of "on-line detection," in the head of production wells, these equipments would present serious disadvantages in compared with the system developed in this invention, such as:
1. Non-intrusive measuring drill. They cannot directly measure the radiation contained in fluid from of the reservoir.
2. They are portable, but with battery life which last from 3 to 10 hrs. which does not allow us to connect them to the wells permanently.
3. They do not have data storage capacity for testing lasting long periods of time (months).
4. Temperature operation is very limited (maximum 55° C.).
5. They do not operate on a autonomous manner, i.e. they require the permanent presence of an operator.

It is worth to say that it have been reported (Zemel, 1995) applications in tracer tests, where it is mentioned that radioactive tracers measurements can be performed in-situ by using detectors NaI (TI), however, features of the measurement system are not specified and even less if they are commercially available equipment, or having similar characteristics to the system of the present invention.

There are also commercial tools or systems (Spectral Gamma Ray Tool, TracerScan, etc.) from different companies like Halliburton, Schlumberger, International Protechnics, etc., whose application is the natural gamma radiation log test, or also gamma spectroscopy applications, within oil wells, these tools are used to characterize the stratums, and they operate at conditions of high temperature and pressure. However, these tools are designed to operate inside the wells, so they do not meet all the features and operating purposes of the measurement system that is result of this invention.

Likewise, with regarding to the above they are published large number of patents relating to tools and systems to make profiles of gamma radiation inside the wells, focusing to different applications. For example, in U.S. Pat. No. 4,007, 366, relate equally to systems and apparatus for take a radiation intensity profile of tracer in different runs that are performed inside the wells. The arrangements consists of a background tool (drill), which has two types of radiation detectors Geiger Müller, a device for injecting a tracer charge inside the well, a telemetry module to transmit data between the drill and the surface equipment. The pulses generated by detectors, are sent to the surface equipment through a cable record. The unit on the surface, has all the postcards for the management of the pulses from the background tool, electronic arrangements for corrections of the readings, discrimination circuits, counters, power supplies to provide the energy needed to power electronic circuits in the equipment fund, etc. Given the characteristics of the detectors used, this system can not differentiate between two or more tracers used, nor can operate autonomously.

Other patents mentioned techniques developed for specific applications related tools also for operate in the interior of the wells, such is the case of U.S. Pat. No. 4,481,597, which refers to an analog to digital converter or spectrum analyzer for use in a drill for making logs of spectrum gamma ray within the wells. The system converts analogics pulses generated by the photomultiplier tube in a digital representation or digital word. This digital representation has the form of numbers representing the energy of gamma rays or other types of nuclear radiation that produces scintillations in the crystal detector, which is optimally coupled to the photomultiplier tube. The digitized value is transmitted by the drill to the surface through cable record.

Also there are published other developments related to the sampling of fluids in wells, as mentioned in the reference U.S. Pat. No. 4,454,772, which describes a new method for automated fluid sampling wells. This method is basically of a series of solenoid valves to inject fluid from the well to a number of sample containers are filled one after another, through the valves that are electrically driven by a programmable switch. Later, with the series of containers collected samples are sent for laboratory analysis. The novelty of the method of the present invention is to automate the sampling of fluid from the wells, thus avoiding moving staff to the sampling points.

The references mentioned above were created for entirely different applications of the present invention, by virtue of this we have implemented an online measurement system of radioactive tracers in the wellhead in an offshore producer of oil, which allows continuously monitor the presence or not presence of three different tracers, above to determine with greater precision the times of arrival of the tracer, while eliminating the need to allocate staff to carry out sampling operations, with all advantages that this represents.

Therefore, one of the objects and advantages of the present invention is to provide a measurement system that allows online monitoring and permanent values of tracer concentration, and is able to operate autonomously according to a program monitoring previously established based on the design and objectives of the injection of tracer to the site, and thus have more data from the tracer activity, which reproduce the response curves of tracer, which contribute to reduce the level of uncertainty and increase efficiency in the analysis and interpretation of results.

BRIEF DESCRIPTION OF THE DRAWINGS OF THE INVENTION

It provide the following FIGS. 1, 2 and 3, in order to understand clearly the online measurement system of radioactive tracer activity in oil fields, and serve as a reference in the application example provided in the following paragraphs. Although the figures illustrate specific provisions of equipment, with which are can go to the practice the present invention, should not be understood as limited to a specific computer.

DETAILED DESCRIPTION OF THE INVENTION

This system object of the present invention was developed with the aim of satisfying the requirements of detection and measurement of the arrival of radioactive tracers that emit gamma radiation, in the head of production wells of oil fields.

Figure 1:
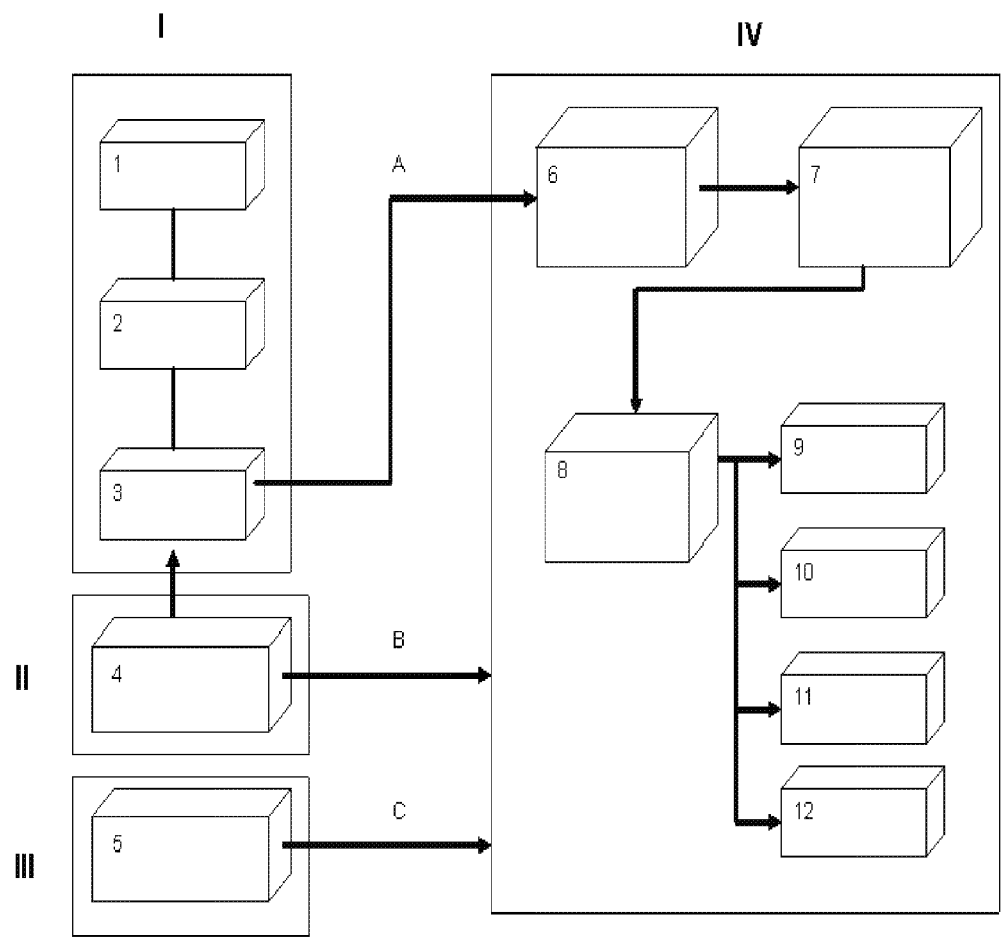
FIG. 1 illustrates a block diagram which shows the parts that make up the online measurement of activity of radioactive tracer in the head in production wells of oil fields, cause for complaint as an innovative system.

In accordance with FIG. 1, the system basically consists of four parts:

I. The radiation detector.
II. The power plant.
III. Laptop.
IV. Data Acquisition Equipment.

The following describes each of the different blocks and their interrelation.

I. Radiation Detector (blocks 1 to 3 of FIG. 1).—This device, as shown in FIG. 1, consists of three elements: the scintillation crystal NaI (TI) and photomultiplier tube (block 2) the high-voltage source (block 1) and an amplifier (block 3). The radiation emitted by the fluid (tracer) from the field, which flows through the container type Marinelli, strike the scintillation crystal, producing flashes to be connected to the photomultiplier tube, is generated out of this a proportional electrical signals the energy of the incident radiation, these pulses generated finally enter the stage of signal amplification. A brief description of each of the three components of the radiation detector:

1) High voltage source (block 1 in FIG. 1).—This is a switching power supply delivering between 1200 and 1500 Volts needed to polarize the photomultiplier tube through a resistive-capacitive arrangement. This source of high-voltage bias required for a direct-current power supply +/−+/−15 Volts, which is provided by a converter AC/DC powered in turn by the solar plant (converters AC/DC).

2) Scintillation crystal and photomultiplier tube (block 2 in FIG. 1).—It is the primary element radiation detector. It is sodium iodide activated with thallium NaI (TI). Cylindrical geometry has a diameter of 2 inches×4 inches long. It chose this type of detector, for the ability to distinguish different energies of radiation, which allows us to differentiate the arrival of several tracers simultaneously. The function of the scintillation crystal is to make the conversion of gamma radiation incident visible electromagnetic energy. The scintillation crystal is coupled photomultiplier tube (PMT), whose function is to convert the electromagnetic energy in the visible region that delivers the scintillation crystal, in pulses of electrical energy. Model was selected photomultiplier used to achieve the coupling of the whole energy range of incident gamma radiation, measurement of 50-2000 keV.

3) Amplifier (block 3 in FIG. 1).—By this module, the pulses are amplified signal from the photomultiplier (PMT). This module is also powered with +/−15 Volts CD.

Features and specifications of the radiation detector, Model: Brand 2GR4/2L-XM Saint-Gobain Crystals:

Dimensions complete radiation detector: 2.37×15.59 inches.

Detector comprising a scintillation crystal, photomultiplier tube, high voltage source and signal amplifier.

Scintillation crystal dimensions: 2×4 inches (diameter, length).

Radiation to be measured: Gamma.

Detection range: 50-2000 keV.

Operating Temperature: 150° C.

Pulse Height Resolution: 7.5% Cs-137.

Material from the cover: Stainless steel.

It is important to mention that the radiation detector was specially designed and built by Saint-Gobain Crystals, according to design specifications and parameters provided by the Tracer Technology Area of the Instituto Mexicano del Petroleo (IMP).

Container radiation detector (represented by number 5 in FIG. 2).—

To increase the efficiency of detection module, we designed a Marinelli container type, stainless steel with an effective volume of 2.3 liters of fluid to reduce undesirable background radiation from the environment, covered container with lead shielding ½ "thick, which allows increasing the minimum level of detection. The container detection module was designed and built to withstand a maximum pressure of 1,600 psi, which is invention is not limited to operate at pressures above this value. This container was designed only for the radiation of Saint-Gobain crystal, which is described here.

II. Power plant (block 4 in FIG. 1). This module is only one component, described below.

4) Power source of the entire system, consisting of a photovoltaic panel, a bank of two batteries, a controller and an inverter DC/AC. With this inverter are generated at 60 Hz 127 volts to power converters, AC/DC Voltage with outputs of +/−15 V, +12 V and +5 V direct current necessary to energize both the radiation detector as other electronic circuitry in the data acquisition module.

The elements that make the solar plant, were selected to allow energy supply to the measuring system, up to 72 hours on days of total darkness. The power supply is permanent on a sunny day or a little sun. Other characteristics of the elements that make up this block are:

Monocrystalline photovoltaic module, is 75 Watts.

PV controller

2 Batteries 100 Amp/hr.

Investor of current.

Converter AC/DC +/−15 Volts and 0.50 Amps output.

Converter AC/DC +5 Volts and 3 Amps output.

III. Laptop (block 5 of FIG. 1). This module has only one component, described below.

5) For programming and retrieval of data acquired during or at the end of the field test carried out. Communication between the device and measuring system, is effected by the protocol via RS-232 serial port at 9600 baud. Similarly, the data processing is performed on this computer. To this end, it was a program in Visual Basic within Excel tool for Microsoft Office.

Through line A in FIG. 1, is performed signal coupling between the power amplifier radiation detector and the entrance to the stage of signal conditioning in data acquisition. Through the communication represented by line B in the figure, power is provided throughout the system, and reading of data stored in the system is done via a laptop computer through a communication port RS-232 (represented by line C of FIG. 1).

IV.—Data Acquisition Equipment (block 6 to 12 in FIG. 1).—Using this equipment, process the pulses from the detection module, has the electronic circuits: signal coupling through a simple differentiating circuit, discrimination pulses with voltage thresholds and timing, a monostable multivibrator and a signal conditioning stage, later entering the counter circuit based on a preset time window, then the data is stored in memory according to the monitoring program established. The information is continuously displayed on a display numbers and as additional support, the information displayed on screen prints.

Here are the main functions of each of the stages that compose the programmable data acquisition equipment and the relation among them, corresponding to blocks 6 to 12, according to FIG. 1:

6) Phase comparison and signal conditioning (block 6 of FIG. 1).—This stage consists of three channels of comparison, earlier in order to be able to detect up to three different radioactive tracer. Each of the comparators is set to an adjustable reference voltage, which corresponds to a detection threshold of the energy of the radiation emitted by the tracer detection is required. Following this section is a monostable multivibrator designed to standardize the width of the pulses to 0.8 us. The purpose of the above, is to avoid problems of overlapping pulses, resulting in erroneous reading would count them. As a protection against noise, which similarly could cause false triggering, the output signal of the previous stage, is coupled through an RC circuit and a gate array to the next stage: the counting of pulses.

7) Step counting of pulses (block 7 of FIG. 1).—As the name implies, this stage is done counting the pulses from the phase comparison and signal conditioning. This has an adjustable time base, allowing count pulses at a frequency of 3.66 msec each to each 8:32 pm. The measuring window was prefixed in 1 minute may count up to 224 pulses, ie 16.78×106 pulses per minute to the time window selected.

8) 16-bit microcontroller (block 8 of FIG. 1).—The integrated microcontroller is used in a development board. Through this device, it performs the function of programming and control, data read from the stage of counting and writing them in memory, as well as the results displayed on screen and printing of the thermal paper. The electronic card microcontroller with a bank of read-only memory (RAM)256 Kbytes, which added to 256 KBytes of internal flash memory that holds the microcontroller, provides a total of 512 Kbytes of user memory that can store approximately 174.000 data. Another feature of the microcontroller, it has ports for 12 C and SPI communication. The latter allow you to link serial devices such as memory, allowing larger data storage capacity of the system to 840.000 or more, if they require the application.

We developed a software in C language, which was compiled, by which the microcontroller performs all control tasks of acquisition, storage and information management.

9) Output interface for the user.—Communication between the user and the microcontroller is done through a keyboard (block 9 of FIG. 1), by which all values are entered the required parameters for programming measurement (frequency counting). As a means of display, it has a liquid crystal display, LCD, and has a thermal printer, as a means of additional support for the information.

The alphanumeric keyboard is 4 columns×4 rows. The display or LCD screen is 4 rows and 16 alphanumeric characters per line. The keyboard is connected to the microcontroller through port H of the microcontroller. This port is configured as input/output (I/O) and LCD display communicates via SPI port.

10) Printer (block 10 of FIG. 1).—As mentioned earlier, to have additional support from the acquired data, joined to the measuring system, a thermal paper printer. Communication between the microcontroller and the thermal printer is done via the serial port at a speed of 9600 baud.

11) Report of data (block 11 of FIG. 1).—This consists of a bank of read-only memory (RAM) 256 Kbytes, which added to 256 KBytes of internal flash memory that holds the microcontroller, gives a total 512 Kbytes of user memory, allowing us to store approximately 174.000 data. The programming is done in the same way paged.

12) The keyboard (block 12 of FIG. 1) is alphanumeric.—4 columns×4 rows. The keyboard is connected to the microcontroller through port H of the microcontroller. This port is configured as input/output (I/O).

Finally, it is noteworthy that the electronic equipment buyer, is contained within a NEMA that protects it from adverse environmental conditions. We should also mention that this computer is powered by alternating current (AC) of 127 Volts and 60 Hz, from the solar plant. This alternating current is converted to direct current of +/−12 Volts and 5 Volts, needed to operate the electronic circuitry above and to polarize the radiation detector. To move from this alternating current to direct current converters used the following AC/DC:

Lambda Converter KWD10-1212 model of +/−12 Volts and 0.45 Amps output.

Converter KWS15 model Lambda-5 +5 Volts and 3 Amps output.

Finally, it is noteworthy that the electronic acquisition equipment, is contained within a NEMA 4 box, which protects it from harsh environmental conditions which must operate. We should also mention that this computer is powered by alternating current (AC) of 127 Volts and 60 Hz, from the solar plant. This alternating current is converted to direct current of +/−15 V, +12 V, needed to operate the electronic circuits mentioned above, as well as providing energy to the detection module. To move from this alternating current to direct current used the following sources of DC power (converters AC/DC) of +/−15 Volts and 0.5 Amps output to +5 Volts, 3 Amps output.

Figure 2:
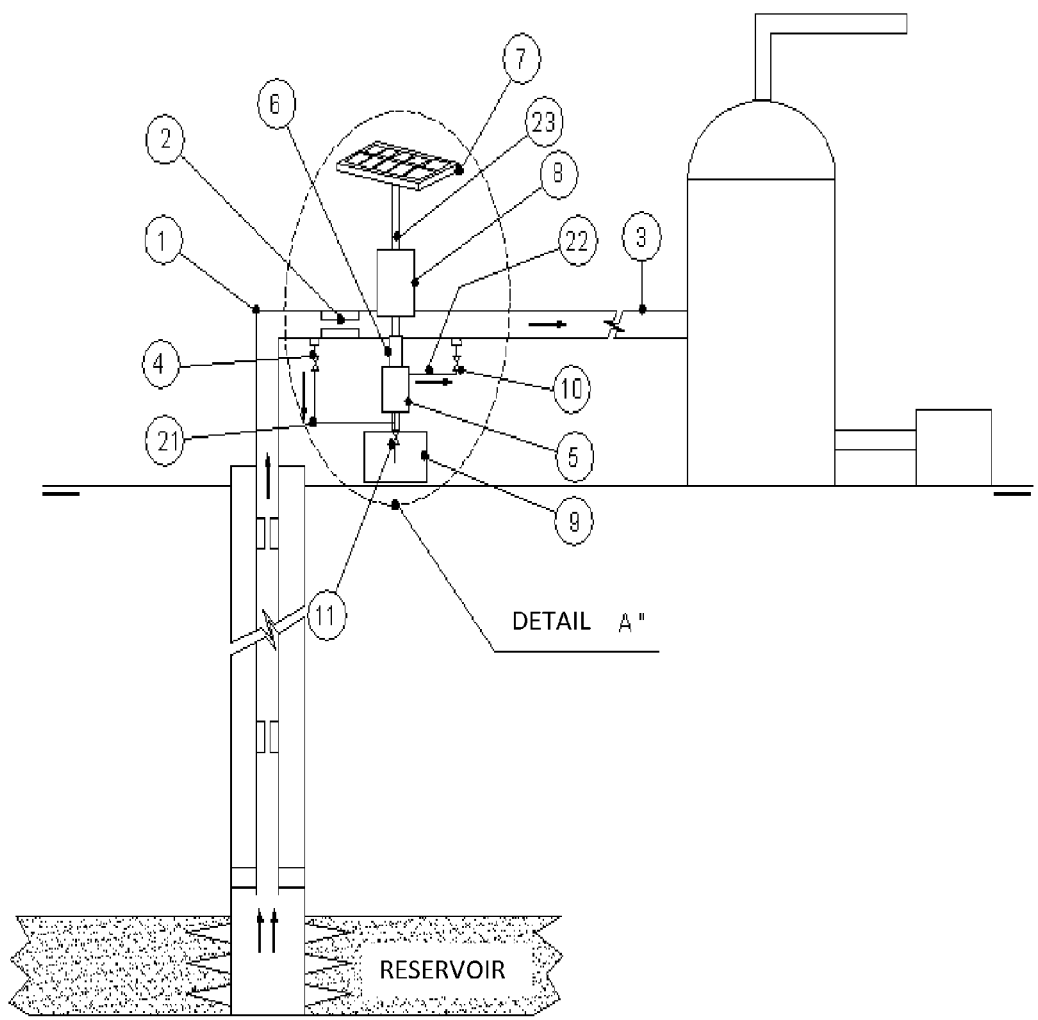
FIG. 2 shows a schematic diagram of the measurement system on-line radioactive tracer, installed between the tubing (before the choke) and Oil Pipe Line (after the choke) in a well in production, at a oil reservoir.
Figure 3:
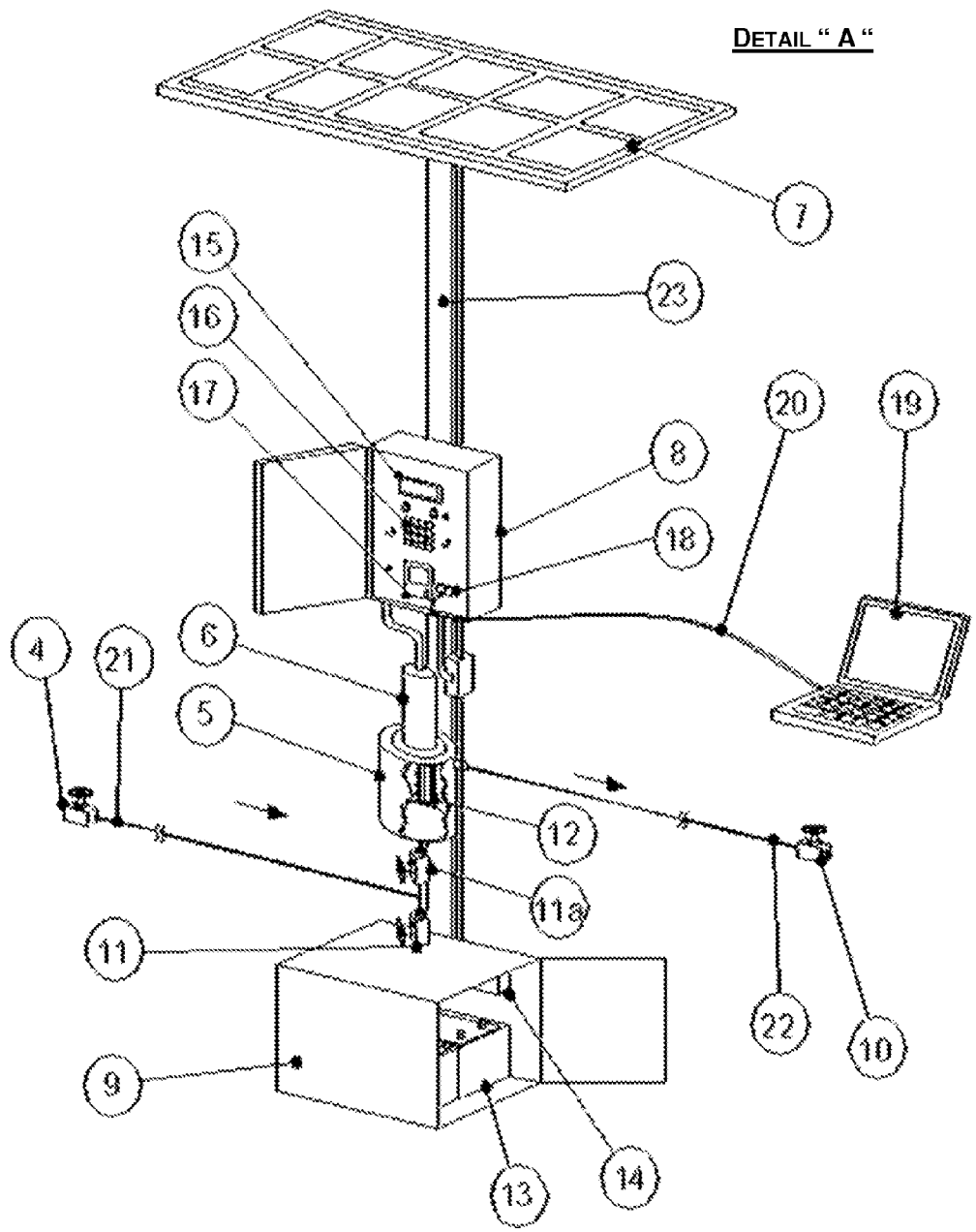
FIG. 3 shows a schematic representation in a greater detail of the measurement system and arrangement of connections required for operation through a bypass flow between the production pipeline and the Oil Pipe Line.

Description of the procedure used for installation and operation measurement system radioactive tracers online at the head of production wells. FIG. 2 and FIG. 3 (Detail A), shows the elements needed to install the equipment on the premises of the production wells in the field under study.

As shown in Detail "A", FIG. 3, the data acquisition system (8), container (5) together with the sensor (12), the battery module (9) and the solar cell (7) are installed on a pipe or pole (23). The container is arranged for coupling mechanical connections and stainless steel tubing or reinforced hose for fluid entry and exit of the container, both the tubing and in which case the hose must withstand the operating pressure and temperature of the well, in one of the wells in which validated the computer, the operating pressure at the well head was 900 psi and the temperature in the head of 119° C. FIG. 2 shows the connection lines (21 and 22), one of them taking well fluid (21), connects before the choke (2), and is fed to the container (5) Valve (4) regulates the flow into the container. The output of the fluid is made by connecting the line (22) to the Oil Pipe Line (3) is tied with the head of the oil collection leading to the separation station. The connection of the line (22) must be made to a valve (10) whether or regulatory step. Normally the valves 4 and 10 are part of an array of valves that are installed on the operating lines of the well and is used for oil sampling and measuring the pressure through mammography manometers installed that monitor operating conditions of both the wellhead and the Oil Pipe Line. In the event that these valves do not exist in this way, you need to install to ensure proper system operation. The container must have installed a valve (11) and a hose for venting and depressurization of the system.

In the implementation phase, first of all must make sure that the solar cell (7), the data acquisition system (8) and all electrical components, are operating properly. You should also ensure that the data acquisition program is scheduled properly considering the duration of the operation. To ensure that the fluid flow on the system of tubing and container must be a difference in pressure between the pressure and the pressure of the Oil Pipe Line. Obviously the pressure at the wellhead must be greater than the pressure of the Oil Pipe Line, on the operational phase it must kept this difference of pressures.

Once installed to the computer as shown in the diagram in FIG. 2, opens the valve (4) to regulate the proper flow, vented in the first instance by the valve (11), having confirmed the flow, closes the valve (11) and opens the valve (10), which the oil is flowed into the system. You should keep a manual record of the variation of pressure from the wellhead and the Oil Pipe Line and if possible the container.

According to FIG. 2, the output interface for the user (Display), communication between the user and the microcontroller is done through a keyboard (16), in which all values are entered the required parameters for the programming of the measurement (frequency count). As a means of display, it has a liquid crystal display, LCD (15), and a thermal printer (17) as a means of additional support information.

As mentioned previously, to have additional support from the acquired data was integrated to the system of measurement, thermal paper printer (17). Communication between the microcontroller and the thermal printer is done via the serial port at a speed of 9600 baud.

Finally, it is noteworthy that the electronic acquisition equipment is contained within a NEMA 4 (8), which protects it from harsh environmental conditions which must operate. We should also mention that this computer is powered by alternating current (AC) of 127 Volts and 60 Hz, from the solar plant.

EXAMPLE

The following example is presented to illustrate the operation of the online measurement system of radioactive tracers in oil well head. This example should not be considered as limiting the claims here, but simply describes the procedure whereby operation tests were performed measuring system online source of this invention, in one of the tests conducted in oil production wells.

We describe useful framework and requirements to which the computer responds developed, and also, a brief description of the measurement system and its main components, the wiring diagram required for testing for the equipment. Referring to FIGS. 2 and 3, have the following:

Description of specialized valves of valves used:
1.) Needle valve ½"—NPT (4) to control the container flow
2.) Needle valve ½"—NPT (10), Security outflow towards the Oil Pipe Line.
3.) Ball valve ½"—NPT (11th) for phase lock control flow.
4.) Needle valve ½"—NPT (11), to purge and depressurization of the system.

Description of operations needed to establish the flow measurement device line tracers: Once installed the system as shown in FIG. 2 and as specified above, the system must be connected before the choke, the will be making fluid and the fluid outlet must be connected to a choke point after on the same line where you have a pressure difference, it is the Oil Pipe Line that reaches the head of collection. Then, it performs the following procedure to enable the operation of the system for online detection of tracers.

FIG. 3 shows the components of the detection system used for the development of operations in the procedure.

Operation 1.—Establishment of Flow
Step 1.—Check that all valves 4, 10, 11*a*, 11 are fully closed.
Step 2.—Check that hose is placed a valve 11 to a storage container vent fluids.
Step 3.—Verify is an instrument for measuring pressure at points of connection, this may be gauge or manografo, in which case you need to install this device.
Step 5.—Manipulating the valve 4, gradually opening it up to a quarter turn around, just as you open the valve 11 regulating the flow slowly to ¼ turn. The valve 11*a* and valve 10 remain closed, maintaining the flow for a term May to 15 seconds, checking the level of container harvesting should be noted that this container will only be used at this stage and in full operation should not be present.
Step 6.—Valve 11 is closed and fully open the valve 11*a*, the valves remain closed 10, which is the conjunction with the Oil Pipe Line of the well. In this step it is suggested to maintain a pressure monitoring system throughout the entire process. In the same manner, it is recommended to verify the existence of unions and fix leaks in such case before making the oil flow on the system.
Step 7.—Gradually opened fully the valve 10, permitting the flow connection to the flow system of the Oil Pipe Line. Establishing the flow and pressure is monitored over a period of time.

Operation 2. Flow Regulation on the Line Feeding the Container
Once flow is established and verified that no leak in the connections necessary to regulate the flow to ensure the movement of fluid in the line and the container.
Step 1.—Check that hose is installed in the valve 11 and it is within the container for collecting fluids from the well.
Step 2.—Check that the valve 11 is closed.
Step 3.—Fully close the valve 11*a*.
Step 4.—Close the valve 4 and then open it slowly to regulate the flow line from the container to the desired flow, making flow measurements over time.
Step 5.—Open slowly until all the valve 11.
Step 6.—Check the volume of container that stores the vent fluid, taking care not to spill.
Step 7.—Verify at any time pressures on the gauges. In this operation, as a first test, the flow was regulated at a cost of 1 liter in 25 seconds; it is noteworthy that output regulation is done at atmospheric pressure where the pressure difference is very high, making the oil flow on the new line of low pressure difference by reducing fluid volume. Once adjusted the flow proceeds to perform the following steps.
Step 8.—Close valve 11.
Step 9.—Check gauge pressure at the head and the Oil Pipe Line.
Step 10.—Open slowly and in full the valve 11*a*, to establish the flow.
Step 11.—Check the setting on the system flow is necessary to consider the motion of fluid in all items of equipment.

Once adjusted, the flow goes to work the system and monitor the pressure data. Table 1 shows an example of data taken in a well where test runs were conducted.

Moreover, it is important to note that the data acquisition system must be programmed to acquire data for as long as the rest of the procedure, and only need to verify that the power supply to work properly, since it depends on energy solar. At this stage of operation, the acquisition system records the energy intensity of the radioactive tracer that is used and is blended in the aqueous phase in the production of hydrocarbon reservoir.

TABLE 1

| | Pressure data with a regulated flow lt/25 seconds | | |
|---|---|---|---|
| Time | Pressure on the wellhead Psi | Pressure gauge 2 (Container) Psi | Pressure Oil Pipe Line connection Psi |
| 13:50 | 890 | 440 | 430 |
| 13:55 | 890 | 440 | 430 |
| 14:00 | 890 | 435 | 430 |
| 17:46 | 890 | 420 | 430 |
| 17:50 | 890 | 450 | 430 |

Operation 3. Depressurization and Purging of the Measuring Equipment
After completing the operations for the detection and measurement of tracer in line at the wellhead, we proceed to disconnect the computer by using the following procedure:
Purge and Depressurization of the System
Step 1.—Check that the valves 4, 10, 11*a* are operating efficiently, the valve 11 must be closed.
Step 2.—Check that the valve 11 hose is placed to a storage container vent fluids.
Step 3.—Manipulating the valve 4, closing gradually until full.
Step 4.—Manipulating the valve 10, closing gradually until full.
Step 5.—Check that the pressure of the wellhead and the Oil Pile Line was reintroduced in its original condition.
Step 6.—11th valve is closed and fully open the valve 11, the remaining fluid should go into the collection container, avoiding spills on the floor. This step is depressurized the line between the wellhead and the container.
Step 7.—Slowly opens in full the valve 11*a*, now allowing the container and the line that goes to the Oil Pipe Line lose pressure.
Step 8.—Verify that the remaining fluid was being removed from the entire system.
Step 9.—Check again that the valves 4 and 10 are closed.
Step 10.—Proceed to disconnect from the production facilities if necessary.

Comments
As part of the results of tests conducted in a well in production, you can mention the following:

The system operates satisfactorily to the conditions of temperature and pressure of 880 psi and 115° C., respectively. It is noted that these conditions are high. Similarly the system is expected to work well under pressure conditions and temperature. Therefore, one can say that the system was tested under extreme conditions.

The system was operating and recording data for a total 53 hours, of which, 15 hrs operated without fluid flow flowing through the container, and 38 hrs from spending registered site.

The different conditions for the tests, without fluids, namely, operating at room temperature, at different costs, allowed to observe and evaluate performance at different operating temperatures.

Conclusions

A summary of some points of tests the equipment:

It was possible to measure the radioactivity (gamma emission) contained in the fluid from the reservoir, connecting such a system between the production tubing Oil Pipe Line and production, i.e., measuring the flow production line and in real time, with a window measuring 1 minus.

The system works perfectly with the operating conditions of the well, the pressure in one case was approximately 900 psi and 450 psi the Oil Pipe Line. Maximum working pressure is by design: 1,600 psi.

The system works fine with the production fluid to a temperature of 115° C. The design is made to withstand a maximum fluid temperature of 150° C.

Autonomy was validated in the measuring system, as to supply its own energy through solar panel and battery assembly. This system is designed to operate continuously and indefinitely.

The system operate continuously 53 hours, is designed to operate on long tests (6 months or more) in terms of data storage capacity is concerned.

Was validated in the field supported by the findings obtained in printed form as well as communication with PC and output data via RS-232 serial port.

The study validated robust heavy duty design capable of withstanding the temperature of the fluid from the reservoir, and environmental conditions of operation of the online measurement system.

It can be highlighted the usefulness of the system of the present invention, in terms of on-line measurement of tracer activity emission range, since this system is not necessary to take samples in the wells to be sent to the laboratory for analysis. The main reason for implementing the system of this invention, it is precisely on-line measuring radioactivity in the fluids from the reservoir, therefore, significantly reduced costs and in particular will more closely in terms of the tracer response curves therefore will increase the reliability of the results of tracer tests also achieved a significant reduction in the costs are normally in the sampling and radiochemical analysis laboratory in a conventional test tracers in oil field.

What is claimed is:

1. An online measuring system of radioactive tracers in an oil well head characterized by being able to autonomously operate and comprising:

(I) a power supply plant for permanent energy supply which is constituted of a photovoltaic panel, a battery bank, a controller and a DC/AC current inverter (direct current/alternating current);

(II) a gamma radiation detection module wherein the NaI scintillation crystal detector (TI) is housed in a stainless steel container of high pressure, through which will continuously flow the fluid samples coming from the well, whose concentration is required to quantify;

(III) a programmable data logger by means of which all operation, control and data management functions are carried out in order to operate system autonomously according to the requirements of each test, constituting by the following stages: a) signal comparison and conditioning, b) pulses counting, c) control and storing and d) interface with the user (data input/output); and (IV) a laptop which has specialized tools as a computer program developed expressly for communication with the logger in order to carry out the following functions;
a) programming of all logging functions, control and storing of data logger;
b) data reading or collection of concentration vs time stored in the memory up to three channels; and
c) data processing, presentation and management.

2. An online measuring system according to claim 1, wherein in order to have sufficient and permanent energy, the supply plant of the electric energy is a solar plant, which is constituted by a photovoltaic panel, a battery bank, a controller and a DC/AC current inverter (direct current/alternating current).

3. An online measuring system according to claim 1, wherein the power sources of direct current are energized through the current inverter and provide voltages of +/−15 Volts and +5 Volts of DC to supply all circuits and electric devices contained in the programmable data logger (discriminators, counters, thermal printer, liquid crystal display), as well as the detection module (photomultiplier tube, high voltage source and amplifier).

4. An online measuring system according to claim 1, wherein the detection module is constituted by: (I) a NaI scintillation crystal detector (TI), and (II) a stainless steel sampling container.

5. An online measuring system according to claim 1, wherein the radiation detector can operate from 0° C. up to a temperature of 150° C. and is constituted by four essential elements: (a) a high voltage source (b) a scintillation crystal, (c) a photomultiplier and (d) an amplifier.

6. An online measuring system according to claim 1, wherein the apparatus (a) includes a high voltage source which energizes the photomultiplier tube with a voltage comprised between 1200 and 1500 Volts.

7. An online measuring system according to claim 1, wherein the paragraph (b) also includes a scintillation crystal made of sodium iodide activated with tallium NaI (TI) whose function is to make the conversion of gamma radiation to visible electromagnetic power.

8. An online measuring system according to claim 1, wherein the paragraph (c) is a photomultiplier tube whose function is to produce an electric signal proportional to the radiation energy incident in the scintillation crystal.

9. An online measuring system according to claim 1, wherein the paragraph (d) includes an amplifier which amplifies the signal pulses coming from the photomultiplier tube (PMT).

10. An online measuring system according to claim 1, wherein the sampling container is made of stainless steel with a cylindrical geometry and is designed to support high pressures.

11. An online measuring system according to claim 1, wherein the sampling container has a cylindrical geometry with a volume capacity of 3.3 liters which is determined based on laboratory experiments where different radioisotopes are used ($^{57}Co$, $^{60}Co$ among others) in tracers' tests.

12. An online measuring system according to claim 1, wherein the sampling container is made of stainless steel and furthermore includes a connection port of the fluid entry line to the container, coming from the production tubing and a connection port of the fluid exit line of the container to the pipeline of the producing well.

13. An online measuring system according to claim 1, wherein the sampling container includes a cover for high pressure made of stainless steel immersed in the sampling volume which isolates and protects the radiation detector (scintillation crystal) of pressure between the production tubing and the pipeline.

14. An online measuring system according to claim 1, wherein the sampling container is made of stainless steel and furthermore includes a leading cover of ½" thickness around all the container acting as a cosmic and environmental radiation shield of the detector.

15. An online measuring system according to claim 1, wherein the sampling container furthermore includes valves and pressure gauges and stainless steel connections of ⅛" of ID: for high pressure through these are connected to the entrance of the sampling container to the valve in the production tubing and the exit of the container to the valve in the pipeline, establishing a pressure differential that circulates the fluid coming from the well through the container.

16. An online measuring system according to claim 1, wherein the paragraph (a) in the Stage II has signal discrimination and conditioning phase for three channels wherein, there are three comparators with adjustable detection thresholds in the discrimination according to the energy of each radioisotope (tracer) used.

17. An online measuring system according to claim 1, wherein the paragraph (a) in the Stage II has signal discrimination and conditioning phase for three channels in each test and furthermore has a monostable multivibrator whose function is to standardize the pulses width and to avoid problems of pulses overlapping.

18. An online measuring system according to claim 1, wherein the paragraph (a) of the Stage III includes a selectable time base to multiples of 1 minute which is performed during the pulses counting coming from one of the channels corresponding to each tracer to be used according to the test operation program, it is possible to program the obtention of concentration readings or measurements from 1 minute to hours depending of the characteristics and needs of the test.

19. An online measuring system according to claim 1, wherein the paragraph (C) of the Stage III contains a 16 bits microcontroller which performs all control, logging, storing and data management functions by means of a previously downloaded program.

20. An online measuring system according to claim 1, wherein the paragraph (c) of the Stage III of data control and management of the logger contains a memory module with a storage capacity of up to 174,000 data.

21. An online measuring system according to claim 1, wherein the paragraph (d) of the Stage III of the logging module of programmable data has a display or alphanumeric screen by means of which the data in real time can be visualized during the test.

22. An online measuring system according to claim 1, wherein the paragraph (d) of the Stage III of the data logger of programmable data has an alphanumeric keyboard of 4 columns per 4 rows through which the user can manually introduce or modify test parameters.

23. An online measuring system according to claim 1, wherein the paragraph (d) of the Stage III of the data logger of programmable data has a thermal printer through which, according to the operation program are registered the performed measurements with the purpose to count on with an additional backup of the measurements carried out during the test.

24. An online measuring system according to claim 1, wherein the Stage III of the data logger includes a cabinet with NEMA 4X specifications, since it is designed in hostile environments where in addition to sealing against dust and water, is resistant to corrosion.

25. An online measuring system according to claim 1, wherein the Stage III has a computer program in a laptop which allows carrying out both programming and data reading of the programmable data logger, i.e. through computers is downloaded in the data logger the operation program and information management.

26. An online measuring system according to claim 1, wherein the communication between the laptop and the data logger is made through the program according to the protocol RS-232 through a serial port.

27. An online measuring system according to claim 1, wherein the paragraph (a) of the Stage III includes the operation program of the measuring system based on the test design downloaded in the data logger through a laptop, complying with the system operation autonomy requirement.

28. An online measuring system according to claim 1, wherein the paragraph (b) of the Stage IV includes the reading function of the data stored in the logger during the test.

29. A method to use the online measuring system according to claim 1, wherein the method comprises the following stages: a) flow establishment; b) flow regulation on the line that supplies the container; c) operation; d) data collection and e) purge and depressurization.

* * * * *